(12) United States Patent
Wood et al.

(10) Patent No.: US 8,372,160 B2
(45) Date of Patent: Feb. 12, 2013

(54) METHOD FOR LEVELLING HAIR COLOUR

(75) Inventors: Jonathan Wood, Weinheim (DE);
Martin Uellner, Darmstadt (DE);
Mustafa Grit, Gernsheim (DE)

(73) Assignee: KPSS-KAO Professional Salon Services GmbH, Darmstadt (DE)

( * ) Notice: Subject to any disclaimer, the term of this patent is extended or adjusted under 35 U.S.C. 154(b) by 0 days.

(21) Appl. No.: 13/382,816

(22) PCT Filed: Jul. 2, 2010

(86) PCT No.: PCT/EP2010/004007
§ 371 (c)(1),
(2), (4) Date: Jan. 6, 2012

(87) PCT Pub. No.: WO2011/003554
PCT Pub. Date: Jan. 13, 2011

(65) Prior Publication Data
US 2012/0102662 A1    May 3, 2012

(30) Foreign Application Priority Data

Jul. 9, 2009    (EP) ..................................... 09008972

(51) Int. Cl.
*A61Q 5/10*    (2006.01)
*A61Q 5/08*    (2006.01)
(52) U.S. Cl. ............. 8/405; 8/431; 424/70.16; 132/202; 132/208
(58) Field of Classification Search ............... 8/405, 431; 424/70.16; 132/202, 208
See application file for complete search history.

(56) References Cited

U.S. PATENT DOCUMENTS

| | | | |
|---|---|---|---|
| 3,590,122 A | 6/1971 | Roberts et al. | |
| 4,486,328 A | 12/1984 | Knott et al. | |
| 5,221,286 A | 6/1993 | Singleton et al. | |
| 5,785,961 A | 7/1998 | Nakama et al. | |
| 6,254,647 B1 | 7/2001 | Froehling | |
| 6,312,677 B1 | 11/2001 | Millequant et al. | |
| 2007/0157399 A1* | 7/2007 | Nobuto et al. | .................... 8/405 |

FOREIGN PATENT DOCUMENTS

| | | |
|---|---|---|
| DE | 24 32 614 A1 | 1/1976 |
| DE | 10 2007 048140 A1 | 4/2009 |
| EP | 1 123 693 A2 | 8/2001 |
| EP | 1 219 285 A | 7/2002 |
| EP | 1 470 812 A | 10/2004 |
| EP | 1 411 885 B1 | 5/2007 |
| EP | 1803436 A1 | 7/2007 |
| FR | 2 920 090 A1 | 2/2009 |
| GB | 1 083 007 A | 9/1967 |
| GB | 2 188 948 A | 10/2004 |
| JP | 2003206221 A | 7/2003 |
| WO | 02/074271 A | 9/2002 |

OTHER PUBLICATIONS

International Search Report Dated Mar. 2, 2011, Mailed Mar. 16, 2011.
International Search Report Dated Mar. 9, 2011, Mailed Mar. 25, 2011.
International Search Report Dated Feb. 15, 2011, Mailed Feb. 25, 2011.
International Search Report Dated Dec. 9, 2010, Mailed Dec. 17, 2010.
English Language Translation of DE2432614 taken from esp@cenet. com, (1976).
International Search Report for PCT/EP2010/004007 dated Mar. 2, 2012.
European Search Report for EP 09008972 dated May 4, 2010.
English abstract for JP2003206221 published Jul. 22, 2003 found on espacenet.

* cited by examiner

*Primary Examiner* — Eisa Elhilo
(74) *Attorney, Agent, or Firm* — Norris McLaughlin & Marcus PA

(57) ABSTRACT

The present invention relates to a method of leveling color of hair comprising applying to the hair a composition resulting from mixing two compositions, A and B, prior to application, wherein composition A is an aqueous composition and comprises at least one oxidizing agent and has an acidic pH, and a composition B is a substantially anhydrous composition and comprises at least one compound with bleaching effect and has a pH between 8 and 12, wherein the application processed for up to 10 min at a temperature between 20 and 45° C. before rinsing and optionally drying steps.

14 Claims, No Drawings

METHOD FOR LEVELLING HAIR COLOUR

This application is a 371 application of PCT/EP2010/004007 filed Jul. 2, 2010, which claims foreign priority benefit under 35 U.S.C. §119 of European Application No. 09008972.3-2108 filed Jul. 9, 2009.

The present invention relates to a method of levelling hair colour, especially lighter coloured hair or including lightened streaks or bleached streaks or bleached as a whole and after certain period of time contrast—difference in colour—between the re-growth and formerly lightened parts is clearly visible.

Making streaks, lightening and bleaching are commonly used hair dressing practices. The aim of such hair dressing services is to get lighter coloured hair parts, or colouring hair to a lighter shade and finally bleaching hair—taking away hair colour as a whole—in order to give attractive appearance. In practice, immediately after such service, consumers' hair has very attractive appearance and naturalness, but this lasts only for a limited period of time because of unattractive contrast between the re-growth and lighter coloured and/or lightened parts by means of bleaching becomes clearly visible. This is especially problem when the uncoloured natural hair is considerably darker, i.e. re-growth has a considerably darker colour than the lighter coloured parts. Colour difference does reduce attractiveness and naturalness and it is highly desirable to give hair attractive colour appearance again without extensive additional chemical treatments. Especially, since such correction is often needed in a relatively short period of time after previous chemical treatment, the corrective treatment must not take a long time, preferably must easily be combinable with other type of hair dressing services, such as and preferably not involving any further chemical treatment. In other words, the corrective treatment should not cause any further damage to the hair or the damage caused by such service should be negligible compared to the damage caused by the previous colouring and/or bleaching.

After a long discussion with hair dressers and the end-user groups, the needs have been clearly identified of such a service. On these bases, various ways have been practiced and surprisingly found out that a levelling service combined with any hair care service is especially suited and it is easily applicable in any hair dressing salons.

It has further been identified that with the existing bleaching products and/or compositions, might be thought suitable for levelling hair colour, cause often dermatological incompatibilities with scalp such as itchiness, redness and scaling reported by volunteers.

Therefore, present invention starts from the problems of effective and easy applicable levelling service wherein the compositions and/or mixtures used for this purpose are mild to skin and do not cause any dermatological incompatibilities.

The inventors of the present invention have surprisingly found out that a substantially anhydrous composition comprising at least one compound with bleaching effect mixed with a composition comprising at least one oxidizing agent and having and acidic pH and applied onto hair and processed for a short period of time levels hair colour effectively and does not cause skin irritation and hair treated with this method has its natural and attractive appearance in terms of colour.

Thus, the first objective of the present invention is a method for levelling colour of hair comprising at least two parts wherein one part being the part not closer to scalp which is artificially colour changed to a lighter colour by means of lightening and/or colouring and/or bleaching than the other part closer to scalp which is preferably undamaged and has its natural colour, wherein hair is optionally shampooed and optionally towel dried and the part directly at the scalp, preferably undamaged and preferably having its natural colour, is applied a composition resulting from mixing two compositions, A and B, prior to application, wherein composition A is an aqueous composition and comprises at least one oxidizing agent and has an acidic pH, preferably between 2 and 5 and composition B is a substantially anhydrous composition and comprises at least one compound with bleaching effect, and composition thus obtained has a pH between 8 and 12, and processed for up to 10 min, preferably between 1 and 8 min, more preferably between 2 and 7 min and most preferably between 2 and 5 min (all values are included) at a temperature between 20 and 45° C., preferably at an ambient temperature and rinsed off from hair and hair is optionally dried.

The second objective of the present invention is a ready to use aqueous composition for levelling hair colour resulting from mixing two compositions, A and B, prior to application onto hair wherein composition A is an aqueous composition and comprises at least one oxidizing agent and has an acidic pH, preferably between 2 and 5, and composition B is a substantially anhydrous composition and comprises at least one compound with bleaching effect, and has a pH between 8 and 12.

Further objective of the present invention is to use of the above composition and method for levelling hair colour.

With the term "levelling" it is meant that hair colour is made more uniform, if not equal, among the parts, preferably between two parts, having different colours wherein one part is artificially colour changed to a lighter colour than its natural colour by means of colouring and/or lightening and/or bleaching either as a whole or only in streaks which is not closer to the scalp and the other part which is closer to the scalp and being undamaged and having darker and preferably natural colour than the remaining part of the hair.

With the phrase "being not closer to the scalp" it is meant the part of hair towards to the tips.

With the phrase "being closer to the scalp" it is meant the hair that has grown since the previous colouration (re-growth) and it is between scalp and colour changed part.

With the term "substantially anhydrous" it is meant that no water is added to the compositions.

It should be noted that the composition, use of it and the method of the present invention is certainly suitable for levelling colour of sun-lightened hair, especially seasonally, and/or age-darkened hair as well.

Throughout the description, the definitions "composition B" and "substantially anhydrous composition" are used interchangeably and have the same meaning.

According to the present invention, the substantially anhydrous composition, composition B, comprises at least one compound with bleaching effect. Suitable compounds are in general peroxides. Useful as such are in particular persulfates such as sodium and potassium persulfate, ammonium persulfate, earth alkali peroxides such as magnesium peroxide, melamine peroxide or urea peroxide or phtholimidoperoxyhexanoic acid, and mixtures thereof. The proportion of peroxides is at least 5%, preferably in the range of 20 to 80%, more preferably 25 to 60% and most preferably 30 to 55% by weight, calculated to total of composition B.

According to the invention, the substantially anhydrous composition can also comprise 0.1% to 10% by weight, calculated to total of composition B, at least one ammonium salts. Suitable ammonium salts are ammonium carbonate, ammonium hydrogen carbonate, ammonium carbamate, ammonium chloride, ammonium sulfate, ammonium phosphates, ammonium nitrate, ammonium bromide, ammonium iodide, ammonium thiosulfate, ammonium molybdate, ammonium vanadate, ammonium sulfamate, ammonium citrate, ammonium salicylate, ammonium valerate, ammonium tartarate, ammonium benzoate, ammonium acetate, ammonium formiate and ammonium lactate. Compositions may also comprise mixture or ammonium salts.

Preferred thereof are the ammonium phosphates, such as ammonium dihydrogen phosphate, ammonium hydrogen phosphate, diammonium sodium phosphate, sodium ammonium hydrogen phosphate, ammonium disodium phosphate, as well as ammonium chloride, ammonium sulphate, diammonium hydrogen citrate, ammonium carbonate, ammonium hydrogen carbonate preferably in an amount from 0.1% to 10% by weight, calculated to total of composition B.

As known from EP 609 796 A2, the ammonium compounds can also be used as sole bleaching agent in respectively higher amounts.

The total proportion of the compounds with bleaching effect preferably ranges from 5% to 85%, preferably 20% to 80%, more preferably 25 to 70% and most preferably 30 to 60% by weight calculated to total of composition B.

In addition to the active component, substantially anhydrous composition also comprises the components customarily used in such compositions: In particular inert pulverulent carrier materials, these are for example, pyrogenic silicium dioxide, starch powder, etc., alkalizing agents, such as sodium metasilicate, surface-active substances, binding agents, etc. In order to avoid repetition, reference is made to the respective standard literature, for example, K. Schrader and A. Domsch, "Cosmetology—Theory and Practice (2005, Verlag für Chemische Industrie), pages 142 to 151.

In a preferred embodiment of the present invention, substantially anhydrous composition is in powder form and in particular it is a dust free powder and comprises oily lipophilic ingredients such as vegetable oils, for example, jojoba oil or any other; petrolatum liquid paraffins, especially paraffinum perliquidum and parafiinum subliquidum; silicone oils; hydropobic fatty acid esters such as octyl palmitate, isocetyl palmitate, isopropyl palmitate and octyl stearate, $C_{10}$- to $C_{36}$-fatty acid triglycerides, as well as their mixtures. In the case that the use is wished among those the most preferred ones are silicone oils, jojoba oil, fatty acid esters, paraffin oils, combinations of fatty acid esters and paraffin oils. Fatty acid esters and/or paraffin oils and/or silicone oils are particularly preferred. Concentration of these oily lipophilic compounds are used in a total amount of about 0.1 to 50% by weight, preferably from 1 to 40% by weight, and more preferably from 2 to 35% by weight, calculated to total of composition B.

In principal any silicone oil is useful as a lipophilic compound. Preferred are dimethicones, dimethiconols and arylated silicones as a lipophilic ingredient at a concentration range of 0.1 to 50%, preferably 0.5 to 40% more preferably 1 to 35% and most preferably 2.5 to 30% by weight calculated to total composition prior to mixing with oxidizing lotion. Non-limiting suitable examples are dimethicones with various viscosity available from Dow Corning under the trade name DC 200, arylated silicones such as phenyl methicone, phenyl trimethicone, diphenyl dimethicone, diphenylsiloxy phenyl trimethicone, tetramethyl tetraphenyl trisiloxane, triphenyl trimethicone, tetramethly tetraphenyl trisiloxane and pentaphenyl trimethyl trisiloxane.

Further, in another preferred form of the invention substantially anhydrous composition comprises polymers from the group consisting of cellulose polymer compounds, alginate, polysaccharides and acrylic acid polymers, preferably methyl cellulose compounds, ethyl cellulose compounds, hydroxyethylcellulose compounds, methylhydroxyethylcellulose compounds, methylhydroxypropylcellulose compounds, carboxymethyl cellulose compounds, alginic acids, sodium alginates, ammonium alginates, calcium alginates, gum arabic, guar gum or xanthan gum, or acrylic acid polymers with molecular weights from about 1,250,000 to 4,000,000, alone or in combination with each other. The polymers are used in a total amount of 0.1 to 15%, preferably from 0.2 to 10%, and more preferably in an amount of from 0.5 to 7.5% by weight, calculated to total of composition B.

Substantially anhydrous composition can also comprise cationic polymers as conditioning and/or thickening agents. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, it has been found suitable those cationic polymers known with their CTFA category name Polyquaternium. Typical examples of those Polyquaternium 1, Polyquaternium 2, Polyquaternium 4, Polyquaternium 5, Polyquaternium 6, Polyquaternium 7, Polyquaternium 8, Polyquaternium 9, Polyquaternium 10, Polyquaternium 11, Polyquaternium 12, Polyquaternium 13, Polyquaternium 14, Polyquaternium 15, Polyquaternium 16, Polyquaternium 17, Polyquaternium 18, Polyquaternium 19, Polyquaternium 20, Polyquaternium 22, Polyquaternium 24, Polyquaternium 27, Polyquaternium 28, Polyquaternium 29, Polyquaternium 30, Polyquaternium 31, Polyquaternium 32, Polyquaternium 33, Polyquaternium 34, Polyquaternium 35 and Polyquaternium 36, Polyquaternium-37, Polyquaternium 39, Polyquaternium 42, Polyquaternium 43, Polyquaternium 44, Polyquaternium 45, Polyquaternium 46, Polyquaternium 47, Polyquaternium 48, Polyquaternium-49, Polyquaternium 50, Polyquaternium 51, Polyquaternium 52, Polyquaternium 53, Polyquaternium 54, Polyquaternium 55, Polyquaternium 56, Polyquaternium 57, Polyquaternium 58, Polyquaternium 59, Polyquaternium 60, Polyquaternium 61, Polyquaternium 62, Polyquaternium 63, Polyquaternium 64, Polyquaternium 65, Polyquaternium 66, Polyquaternium 67, Polyquaternium 68, Polyquaternium 69, Polyquaternium-70, Polyquaternium 71, Polyquaternium 72, Polyquaternium 73, Polyquaternium 74, Polyquaternium 75, Polyquaternium 76, Polyquaternium 77, Polyquaternium 78, Polyquaternium-79, Polyquaternium 80, Polyquaternium 81, Polyquaternium 82, Polyquaternium 83, Polyquaternium 84, Polyquaternium 85, Polyquaternium 86 and Polyquaternium 87.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-82, Quaternium-83 and Quaternium-84.

Typical concentration range for any of the cationic conditioners mentioned above can be 0.1-7.5% by weight, preferably 0.3-5% by weight and more preferably 0.5-2.5% by weight, calculated to total of composition B.

Substantially anhydrous composition of the present invention may comprise at least one dialkyl carbonate of general formula $$R_1OC(O)OR_2$$

where $R_1$ and $R_2$ are independent from each other linear or branched saturated alkyl chains with 6 to 22 C atoms.

Preferred at least one dialkyl carbonate is selected from di(caprylyl) carbonate and di(ethylhexyl) carbonate.

Concentration of at least dialkyl carbonate may vary between 0.1 and 30% by weight calculated to total of composition B.

Substantially anhydrous compositions of the present invention can comprise synthetic mica coated with metal oxide or oxides having a volume particle size distribution in the range of 1 to 750 μm. Use of synthetic mica coated with metal oxide or oxides mainly in decorative cosmetics is disclosed in an international patent application of Sun Chemical Corporation published with a number WO 2005/065632 A1. In the document synthetic mica and coated synthetic mica with at least one metal oxide or oxides is disclosed in detail. The content of the document is included herewith by reference.

Suitable metal oxide or oxides for coating synthetic mica are titanium dioxide, chromium oxide, ferric oxide or mixtures thereof. In the present invention the preferred is synthetic mica coated with titanium dioxide. Such materials are commercially available from Sun Chemical Corporation and Merck (Timiron Synwhite 40) and known with their INCI names Synthetic Fluorphologopite The volume particle size distribution of synthetic mica coated with a metal oxide or oxides is in the range of 1 to 750 μm, preferably 1 to 250 μm, more preferably 1 to 100 μm and most preferably 5 to 95 μm. The particle sizes referred are relating to the volume particle size distribution meaning that particles found in the coated synthetic mica having volume particle size in the given ranges.

Concentration of synthetic mica coated with at least metal oxide or oxides is from 0.01 to 20%, preferably 0.1 to 15%, more preferably 0.25 to 10% and most preferably 0.5 to 55% by weight calculated to total of composition B.

Pigments may be part of the composition B such as various types of ultramarines know under the technical names ultramarine, ultramarine blue, ultramarine green, ultramarine pink, ultramarine red, ultramarines, ultramarine violet and cosmetic ultramarine blue according to Cosmetic Ingredient Dictionary. As the compounds generally used for colouring the substantially anhydrous powder composition their concentration is as low as 0.0001% and may be as high as 0.1% by weight calculated to total of composition B.

Substantially anhydrous composition comprises preferably at least one calcium salt. Both organic and inorganic ones are suitable for the purpose of the present invention. Inorganic salts are most preferred. Suitable calcium salts are calcium aluminium borosilicate, calcium aspartate, calcium benzoate, calcium acetate, calcium carbonate, calcium citrate, calcium dihydrogen phosphate, calcium fluoride, calcium hydroxide, calcium lactate, calcium monofluorophosphate, calcium oxide, calcium phosphate, calcium propionate, calcium pyrophosphate, calcium sulphate, calcium nitrate, calcium salicylate, calcium silicate, hydrate, calcium tartarate, tricalcium phosphate, calcium chloride, calcium iodide and calcium bromide. Preferred are calcium benzoate, calcium acetate, calcium carbonate, calcium citrate, calcium dihydrogen phosphate, calcium fluoride, calcium hydroxide, calcium lactate, calcium monofluorophosphate, calcium oxide, calcium phosphate, calcium propionate, calcium pyrophosphate, calcium sulphate, calcium nitrate, calcium salicylate, calcium silicate, hydrate, calcium tartarate, tricalcium phosphate, calcium chloride, calcium iodide and calcium bromide. More preferred calcium acetate, calcium carbonate, calcium citrate, calcium dihydrogen phosphate, calcium fluoride, calcium hydroxide, calcium lactate, calcium oxide, calcium phosphate, calcium propionate, calcium pyrophosphate, calcium sulphate, calcium nitrate, calcium silicate, calcium tartarate, calcium chloride, calcium iodide and calcium bromide. The most preferred are calcium carbonate, calcium dihydrogen phosphate, calcium fluoride, calcium hydroxide, calcium oxide, calcium phosphate, calcium pyrophosphate, calcium sulphate, calcium nitrate, calcium chloride, calcium iodide and calcium bromide. Calcium sulphate is particularly preferred because of its outstanding effect.

Concentration of at least one calcium salt in substantially anhydrous composition is between 0.1 and 20%, preferably between 0.5 and 15%, more preferably between 0.75 and 10% and most preferably between 1 and 7.5% by weight calculated to total of composition B.

Substantially anhydrous composition can be in any form such as a solution, dispersion, suspension and powder. Preferred is a powder form and most preferably it is a dust free powder.

The average particle size of the dust free bleaching powder composition according to the invention is generally range below 1 mm, preferably below 500 μm, more preferably less than 400 μm and in particular about 25 to about 100 μm, thus ensuring excellent processing capability, i.e. miscibility with an aqueous hydrogen peroxide solution prior to application onto human hair.

The powder composition can be produced with processes such as by mixing the powder ingredients first and subsequently adding lipophilic ingredient(s) and by fluidized bed method. In fluidized bed method, powder ingredients are mixed in a vessel and made flowing by inletting an air flow which may be heated (preferred when using waxy component) or carried out at room (ambient) temperature and while the powder mix freely "flowing" lipophilic ingredient and/or mixture with any other liquid component is sprayed from a nozzle mounted above the powder batch.

Composition A is an aqueous composition and comprises at least one oxidizing agent. The oxidizing agents suitable are hydrogen peroxide, urea peroxide, melamin peroxide or perborate salts. The most preferred is hydrogen peroxide. Such composition comprises 0.5 to 6% by weight calculated to total of composition A.

Composition A comprises additionally and preferably one or more surfactants selected from non-ionic, anionic, amphoteric and cationic ones preferably at a concentration between 0.1 to 15%, preferably 0.5 to 10%, more preferably 1 to 7.5% by weight calculated to total of composition A. The concentration ranges mentioned here refer to the total surfactant concentration in the composition A.

Suitable non-ionic surfactants are alkyl polyglucosides of the general formula

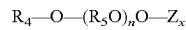

$R_4$—O—$(R_5O)_n$O—$Z_x$ wherein $R_4$ is an alkyl group with 8 to 18 carbon atoms, $R_5$ is an ethylene or propylene group, Z is a saccharide group with 5 to 6 carbon atoms, n is a number from 0 to 10 and x is a number between 1 and 5. Examples are decyl glucoside, carpylyl glucoside, ceteary glucoside, cocoyl ethyl glucoside, lauryl glucoside, myristyl glucoside and coco glucoside. Preferred are decyl glucoside and coco glucoside which are commercially available with the trade name Plantacare from the company Cognis.

Further non-ionic surfactants suitable are long-chain fatty acid mono- and dialkanolamides according to the general structure

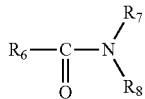

wherein $R_6$ is an alkyl chain which may be saturated or unsaturated, straight or branched, substituted or unsubstituted with a length of 8 to 22 C atoms, preferably 10 to 18 and more preferably 12 to 18 C atoms, $R_7$ and $R_8$ are same or different H, $C_1$ to $C_4$ alkyl or hydroxyl alkyl, preferably $C_2$ hydroxy alkyl with the condition that at least one of the $R_7$ and $R_8$ is not H.

Suitable non-limiting examples are behenoyl monoethanolamide, coco monoethanolamide, isostearoyl monoethanolamide, lauroyl monoethanolamide, myristoyl monoethanolamide, oleoyl monoethanolamide, ricinoleoyl monoethanolamide, stearoyl monoethanolamide, behenoyl diethanolamide, caproyl diethanolamide, cocoyl diethanolamide, isostearoyl diethanolamide, lauroyl diethanolamide, lineloyl monoethanolamide, myristoyl monoethanolamide, oleoyl monoethanolamide, palmitoyl diethanolamide, ricinoleoyl monoethanolamide and stearoyl monoethanolamide, Further additionally useful non-ionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®".

Another type of non-ionic surfactants and the preferred ones are $C_{10}$-$C_{22}$-fatty alcohol ethoxylates. Especially suited are $C_{10}$-$C_{22}$-fatty alcohol ethers with the average degree of ethoxylation between 1 and 25, preferably 2 and 20, more preferably 2 to 10. Suitable examples are oleth-2, oleth-3, oleth-4, oleth-5, oleth-6, oleth-7, oleth-8, oleth-9, oleth-10, oleth-11, oleth-12, oleth-15, oleth-16, oleth-20, oleth-25, laureth-2, laureth-3, laureth-4, laureth-5, laureth-6, laureth-7, laureth-8, laureth-9, laureth-10, laureth-11, laureth-12, laureth-13, laureth-15, laureth-16, laureth-20, laureth-25, ceteth-10, ceteth-12, ceteth-14, ceteth-15, ceteth-16, ceteth-17, ceteth-20, ceteth-25, cetoleth-10, cetoleth-12, cetoleth-14, cetoleth-15, cetoleth-16, cetoleth-17, cetoleth-20, cetoleth-25, ceteareth-10, ceteareth-12, ceteareth-14, ceteareth-15, ceteareth-16, ceteareth-18, ceteareth-20, ceteareth-22, ceteareth-25, isosteareth-10, isosteareth-12, isosteareth-15, isosteareth-20, isosteareth-22, isosteareth-25, steareth-10, steareth-11, steareth-14, steareth-15, steareth-16, steareth-20, and steareth-25.

Further suitable non-ionic surfactants are glyceryl fatty acid esters according to the general formula

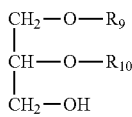

wherein $R_9$ and $R_{10}$ are same or different H, or a fatty acid group which may be saturated or unsaturated, branched or straight, substituted or unsubstituted with a C number between 10 and 22 with the condition at least one of the $R_9$ and $R_{10}$ is a fatty acyl group. The esters according the above general structure has preferably C number between 12 and 18 and more preferably 14 and 18. In particular glyceryl steric acid esters are preferred.

Most preferred glyceryl fatty acid esters are glyceryl stearate and glyceryl distearate.

Further non-ionic surfactants within the meaning of the present invention are polyalkyleneglycol ether of fatty acid glyceride or partial glyceride with at least 20 polyalkylene units, especially with 20 to 150, more preferably 20 to 100, most preferably 30 to 75 polyethyleneglycol units. Examples to those are PEG-30 hydrogenated castor oil, PEG-35 hydrogenated castor oil, PEG-40 hydrogenated castor oil, PEG-45 hydrogenated castor oil, PEG-50 hydrogenated castor oil, PEG-55 hydrogenated castor oil, PEG-60 hydrogenated castor oil, PEG-65 hydrogenated castor oil, PEG-80 hydrogenated castor oil, PEG-100 hydrogenated castor oil, PEG-200 hydrogenated castor oil, PEG-35 castor oil, PEG-50 castor oil, PEG-55 castor oil, PEG-60 castor oil, PEG-80 castor oil, PEG-100 castor oil. Additional examples of similar compounds can be found in the cosmetic ingredient dictionaries and cosmetic textbooks.

Further suitable non-ionic surfactants within the meaning of present invention are glycol fatty acid esters according to the general structure

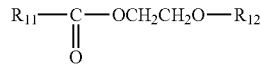

wherein $R_{11}$ is a saturated or unsaturated, branched or straight, substituted or unsubstituted alkyl with a 9 to 21 C atoms and $R_{12}$ is H or a saturated or unsaturated, branched or straight, substituted or unsubstituted acyl with 10 to 22 C atoms.

Suitable non-limiting examples are glycol cetearate, glycol dibehenate, glycol dilaurate, glycol dioleate, glycol stearate, glycol distearate, glycol oleate, glycol palmitate, glycol ricinoleate, and glycol stearate SE. Most preferred are glycol stearate SE, glycol stearate and glycol distearate.

Further suitable non-ionic surfactants are non-ionic silicone surfactants Preferred silicone surfactants are ethoxylated and/or propoxylated dimethicones. Non-limiting suitable examples are PEG/PPG 3/10 dimethicone, PEG/PPG 4/12 dimethicone, PEG/PPG 6/4 dimethicone, PEG/PPG 6/11-dimethicone, PEG/PPG 8/14 dimethicone, PEG/PPG 8/26 dimethicone, PEG/PPG 12/16 dimethicone, PEG/PPG 12/18 dimethicone, PEG/PPG 15/15 dimethicone, PEG/PPG 17/18 dimethicone, PEG/PPG 18/12 dimethicone, PEG/PPG 18/18 dimethicone, PEG/PPG 19/19 dimethicone, PEG/PPG 15/20 dimethicone, PEG/PPG 20/20 dimethicone, PEG/PPG 20/23 dimethicone, PEG/PPG 20/29 dimethicone, PEG/PPG 22/23 dimethicone, PEG/PPG 22/24 dimethicone, PEG/PPG 25/25 dimethicone, PEG/PPG 27/27 dimethicone, PEG/PPG 20/29 dimethicone and PEG/PPG 20/29 dimethicone.

Among the non-ionic surfactants mentioned above fatty alcohol ethoxylates and fatty acid glyceryl esters and glycol fatty acid esters and their mixtures at any weight ratio are the most preferred ones.

Nonlimiting suitable examples of anionic surfactants are the sulfate, sulfonate, carboxylate and alkyl phosphate type, especially, of course, those customarily used $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates and their salts.

Particular reference is made to the fatty alcohol ether sulfates of the general structure

wherein $R_{14}$ is a saturated or unsaturated, straight or branched, substituted or unsubstituted alkyl chain with 10 to 18 C atoms, n is from 1 to 5 and M is a cation, preferably ammonium, sodium or potassium.

Suitable examples are ammonium capryleth sulphate, ammonium C12-15 pareth sulphate, ammonium laureth sulphate, ammonium laureth-5 sulphate, ammonium myreth sulphate, DEA C12-13 pareth-3 sulphate, DEA laureth sulphate, DEA myreth sulphate, diethylamine laureth sulphate, magnesium coceth sulphate, magnesium laureth sulphate, magnesium laureth-5 sulphate, magnesium myreth sulphate, magnesium oleth sulphate, MEA laureth sulphate, MIPA C12-15 pareth sulphate, MIPA laureth sulphate, sodium coceth sulphate, sodium C9-15 pareth-3 sulphate, sodium C10-15 pareth-3 sulphate, sodium C12-16 pareth-2 sulphate, sodium C12-13 pareth sulphate, sodium C12-14 pareth-3 sulphate, sodium C12-15 pareth sulphate, sodium C12-15 pareth-3 sulphate, sodium C13-15 pareth-3 sulphate, sodium doceth sulphate, sodium laneth sulphate, sodium laureth sulphate, sodium laureth-5 sulphate, sodium myreth sulphate, sodium oleth sulphate, TEA laureth sulphate, TEA laneth sulphate and TIPA laureth sulphate.

Further anionic surfactants of the carboxylate type are alkyl polyether carboxylic acids and the salts thereof of the formula

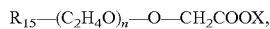

wherein $R_{15}$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

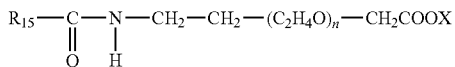

wherein $R_{15}$ and X have the above meanings, and n is in particular a number from 1 to 10, preferably 2.5 to 5.

Further suitable anionic surfactants are also $C_8$-$C_{22}$-acyl aminocarboxylic acids or the water-soluble salts thereof. Suitable ones are N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

Among the anionic surfactants most preferred are alkyl sulfates and/or alkyl ether sulfates and among them sodium lauryl or laureth sulfates and their mixtures are most preferred.

Amphoteric surfactants may be part of the Composition A. Useful are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

In detail, it is possible to use betaines of the structure

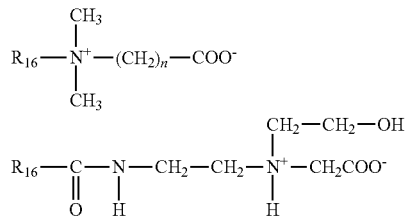

wherein $R_{16}$ is a $C_8$-$C_{18}$-alkyl group and n is 1 to 3; sulfobetaines of the structure

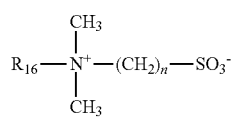

wherein $R_{16}$ and n are same as above; and amidoalkyl betaines of the structure

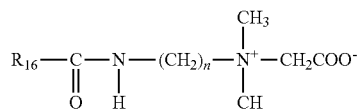

wherein $R_{16}$ and n are same as above.

Suitable nonlimiting examples are almondamidopropyl betaine, apricotamidopropyl betaine, avocadoamidopropyl betaine, babasuamidopropyl betaine, behenamidopropyl betaine, cocamidopropyl betaine, lauramidopropyl betaine, myristylamidopropyl betaine, oleamidopropyl betaine, olivamidopropyl betaine, palmamidopropyl betaine, palmitamidopropyl betaine, ricinoleamidopropyl betaine, sesamamidopropyl betaine, soyamidopropyl betaine, stearamidopropyl betaine, behenyl betaine, cetyl betaine, myristyl betaine, lauryl betaine, coco betaine, decyl betaine, oleyl betaine, stearyl betaine, tallow betaine, cocamidopropyl hydroxysultaine, coco hydroxysultaine, coco sultaine, lauramidopropyl hydroxysultaine, lauryl hydroxysultaine, myristamidopropyl hydroxysultaine, oleamidopropyl hydroxysultaine and lauryl sultaine Preferred amphoteric surfactants are of betaine types such as coco betaine and cocoylamidpropyl betaine.

Composition A may further comprise one or more cationic and/or cationizable surfactants with the general formula

wherein $R_{17}$ is a saturated or unsaturated, straight or branched alkyl group with 8 to 24 C atoms, $R_{18}$ is a straight or branched alkyl group with 1 to 4 C atoms, A is a group selected from O,

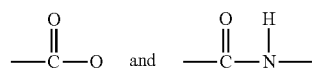

and B is selected from

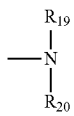

wherein $R_{19}$ and $R_{20}$ are the same or different is H or an alkyl with 1 to 4 C atoms, hydroxyl alkyl with 1 to 4 C atoms and di hydroxyl alkyl with 2 to 4 C atoms,

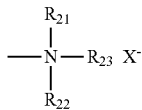

$R_{21}$, and $R_{22}$ are the same or different, an alkyl with 1 to 4 C atoms, hydroxyl alkyl with 1 to 4 C atoms and di hydroxyl alkyl with 2 to 4 C atoms, $R_{23}$ is an alkyl with 1 to 4 C atoms, hydroxyl alkyl with 1 to 4 C atoms or di hydroxyl alkyl with 2 to 4 C atoms and

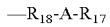

wherein $R_{17}$, A and $R_{18}$ have the above meaning and X is chloride, bromide, methosulfate, or a quaternary ammonium surfactant according to the general formula

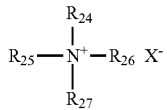

where $R_{24}$ is a saturated or unsaturated, branched or non-branched alkyl chain with 8-24 C atoms and $R_{25}$ is unsaturated or saturated, branched or non-branched alkyl chain with 1-24 C atoms and $R_{26}$ and $R_{27}$ are lower alkyl chain with 1 to 4 carbon atoms which may be substituted with one or more hydroxyl groups, and X is anion such as chloride, bromide, methosulfate.

Non-limiting suitable examples are stearyloxypropyl amine, palmityloxypropyl amine, stearyloxypropyldimethyl amine, stearyloxypropyldiethyl amine, stearyloxyethylyldimethyl amine, stearyloxyethyl amine, myristyloxypropyl amine, myristyloxypropyldimethyl amine, palmitamidopropyl amine, palmitamidopropyl methylamine, palmitamidopropyl diethylamine, palmitamidopropyl dibutylamine, palmitamidopropyl buylamine, palmitamidopropyl dipropylamine, palmitamidopropyl propylamine, palmitamidopropyl dihydroxyethylamine, palmitamidopropyl hydroxyethylamine, palmitamidopropyl dihydroxypropylamine, palmitamidopropyl hydroxypropylamine, lauramidopropyl amine, lauramidopropyl methylamine, lauramidopropyl diethylamine, lauramidopropyl dibutylamine, lauramidopropyl buylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearamidopropyl methylamine, stearamidopropyl diethylamine, stearamidopropyl dibutylamine, stearamidopropyl buylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibehenamidopropyl propylamine, dibehenamidopropyl hydroxyethylamine, palmitoamidopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palmitoylpropyl amine, palmitoylpropyl methylamine, palmitoylpropyl diethylamine, palmitoylpropyl dibutylamine, palmitoylpropyl buylamine, palmitoylpropyl dipropylamine, palmitoylpropyl propylamine, palmitoylpropyl dihydroxyethylamine, palmitoylpropyl hydroxyethylamine, palmitoylpropyl dihydroxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, behenylpropyl amine, behenylpropyl methylamine, behenylpropyl diethylamine, behenylpropyl dibutylamine, behenylpropyl butylamine, behenylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, dibehenylpropyl hydroxyethylamine, palmitylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulfate, dicocoylethylhydroxyethylmonium methosulfate, cetyltrimethyl ammonium chloride, steartrimonium chloride, behentrimonium chloride, myristyltrimethyl ammonium chloride, distearyldimethyl ammonium chloride, and dibehenyldimethyl ammonium chloride.

Composition A may further comprise one or more fatty alcohol of the general formula $$R_{13}-OH$$

wherein $R_{13}$ is a linear or branched, saturated or unsaturated, substituted or unsubstituted alkyl chain with 12 to 22 C atoms.

Suitable fatty alcohols are myristyl alcohol, cetyl alcohol, stearyl alcohol and behenyl alcohol and their mixtures. Most preferred is the mixture of cetyl and stearyl alcohol also known as cetearyl alcohol.

The concentration of one or more fatty alcohols is in the range of 0.1 to 10%, preferably 0.5 to 7.5%, more preferably 0.5 to 5% and most preferably 1 to 5% by weight calculated to total of composition A.

Composition A may further comprise oily substances selected from such as silicone oils, either volatile or non-volatile, natural and synthetic oils. Among silicone oils those can be added to the compositions include dimethicone, dimethiconol, polydimethylsiloxane, DC fluid ranges from Dow Corning, as well as aminated silicones such as amodimethicone, aminopropyl phenyl trimethicone; arylated silicones with one to 5 phenyl groups in its molecule such as trimethylpentaphenyl trisiloxane, phenyl trimethicone, triphenyl trimethicone and cyclic siloxanes such as cyclomethicone, cyclotrisiloxane, cyclopentasiloxane, cycloheptasiloxane and cyclotrisiloxane. Natural oils such as olive oil, almond oil, avocado oil, wheatgerm oil and ricinus oil may be included in the composition A.

Synthetic oils may be included in composition A as conditioning agent such as mineral oil, alkyl esters of fatty acids such as isopropyl myristate, palmitate, stearate and isostearate, oleyl oleate, isocetyl stearate, hexyl laurate, dibutyl adipate, dioctyl-adipate, myristyl myristate and oleyl erucate.

Further polyols may be included in the composition A such as glycerin, glycol and derivatives, polyethyleneglycols known with trade names Carbowax PEG from Union Carbide and Polyox WSR range from Amerchol, polyglycerin, polyethyleneglycol mono or di fatty acid esters having general formula $$R_{28}CO(OCH_2CH_2)_nOH \text{ or}$$

$$R_{28}CO(OCH_2CH_2)_nOOCR_{29}$$

where $R_{28}$ and $R_{29}$ are independent from each other saturated, unsaturated or branched or non-branched alkyl chain with 7 to 21 C atoms and n is typically 2-100.

The composition A may also comprise further protein hydrolyzates and polypeptides, e.g., keratin hydrolyzates, collagen hydrolyzates of the type "Nutrilan®" or elastin hydrolyzates, as well as also in particular plant protein hydrolyzates, optionally, cationized protein hydrolyzates, e.g., "Gluadin®".

Additional natural plant extracts can as well form part of the composition A of the present invention. Suitable aqueous (e.g. steam-distilled) alcoholic or hydro-alcoholic plant extracts known per se are in particular extracts from leaves, fruits, blossoms, roots, rinds or stems of aloe, pineapple, artichoke, arnica, avocado, valerian, bamboo, green tea, blue lotus flower, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, coconut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc.

Suitable trade products are, for example, the various "Extrapone" products and "Herbasol®". Extracts and the preparation thereof are also described in "Hagers Handbuch der pharmazeutischen Praxis", $4^{th}$ Ed.

The composition A can comprise one or more organic solvents such as ethanol. propanol, isopropanol, benzyl alcohol, benzyloxyethanol, alkylene carbonates such as ethylene carbonate and propylene carbonate, phenoxyethanol, butanol, isobutanol, cyclohexane, cyclohexanol, hexyleneglycol, ethylenecarbonate, ethyleneglycol monoethylether, ethylene glycol monobutyl ether, ethylene glycol monophenyl ether, 1-phenylethylalcohol, 2-phenylethylalcohol, o-methoxyphenol. Concentration of organic solvent can be in the range of 1 to 40%, preferably 1 to 25% by weight, calculated to total of composition A.

It should be noted that for levelling hair colour within the meaning of the present invention, hair dyes are not required, especially when this is done on a previously partly or as a whole bleached hair.

On the other hand, in principal, direct dyes may be included in the composition B of the present invention.

Suitable ones are direct dyes of neutral, cationic and anionic character. Some examples to suitable cationic dyes are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 51, Basic Red 76, Basic Violet 1, Basic Violet 2, Basic Violet 3, Basic Violet 10, Basic Violet 14 and Basic Yellow 57. According to the invention, suitable cationic dyestuffs are in principal those any available on the market for cosmetic hair colouring applications. For this purpose, special reference is made to the PCT application WO 95/15144 of Ciba-Geigy AG. The content of the PCT application WO 95/15144 is by reference incorporated here.

Examples to suitable direct acting anionic dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Some examples to those suitable neutral dyes (HC dyes), so called nitro dyes, are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

The compositions A and/or B may further comprise an organopolysiloxane compound wherein at least one silicon atom is linked to an alkylene group having a hetero-atom, in particular a nitrogen atom, with a poly-(N-acyl alkyleneimine) units of the formula

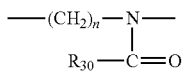

wherein n is a number from 1 to 5 and $R_{30}$ is hydrogen, a $C_1$-$C_{12}$-alkyl or cycloalkyl, aralkyl or aryl group.

Preferred organopolysiloxane polymers are those of the type disclosed in EP-A 640 643, in particular optionally quaternized aminoalkyl, in particular aminopropyl dimethyl polysiloxane/polyethyl oxazoline copolymers of the formula

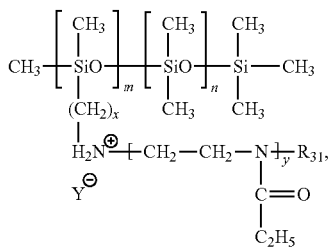

wherein m and n each are numbers from 20 to 10,000, in particular 50 to 7,000, especially 100 to 5,000, x is a number between 1 and 5, preferably 3, and y is a number from 5 to 30, $R_{31}$ is a $C_1$-$C_{12}$-alkyl or aryl group, in particular a methyl, ethyl or benzyl group, and $Y^-$ is an anion.

Especially suited are the organopolysiloxanes disclosed under the terms A-1, A-2 and A-3 on pages 12 to 13 of EP-A 640 643. The proportion of graft copolymers in the hair colouring compositions according to the invention ranges from 0.05% to 5%, preferably 0.1% to 2.5%, in particular 0.5% to 1.5% by weight, calculated to the total composition.

Another compound that may be comprised in the composition A and/or B is a ceramide type of compounds according to the general formula

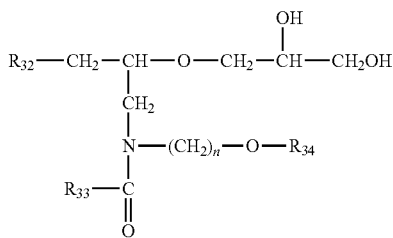

wherein $R_{32}$ and $R_{33}$ are independent from each other alkyl- or alkenyl group with 10 to 22 carbon atoms, $R_{34}$ is methyl, ethyl, n-propyl or isopropyl group and n is a number between 1 to 6, preferably 2 or 3. The concentration of the ceramide type of compound in colouring compositions of the present invention can be in the range of 0.01 to 2 and especially 0.01 to 1% by weight calculated to the total composition.

Preferred ceramide compound is cetyl-PG-hydroxyethylpalmitamide.

Sterols, especially the phytosterols, may as well be comprised in Compositions A and/or B. Suitable ones are especially of plant origin for example ergosterol, sitosterol, stigmasterol, fucosterol, brassicasterol, fungisterol, campesterol, zymosterol, ascosterol, cerevisterol, episterol, faecosterol, spinasterol.

The concentration of ceramide may be in the range of 0.01 to 2% and phytosterol may be comprised in the range of 0.01 to 0.5% by weight calculated to the total of composition A or B.

The compositions A and/or B may further comprise one or more ubiquinone of the formula.

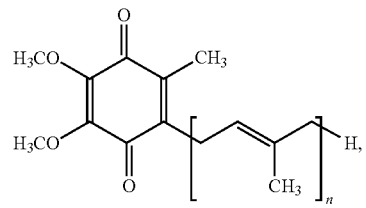

wherein n is a number from 1 to 10. The concentration of ubichinones in the compositions of the present invention can vary between 0.001% and 10% by weight, calculated to the total composition excluding the oxidizing agent.

Further compositions A and/or B can comprise yogurt powder at a concentration of 0.01 to 5% by weight calculated to total of the compositions A or B, which is a raw material prepared by spray drying of natural yoghurt after completion of fermentation. Yogurt powder comprises the following major components:
  approximately 53.5% lactose,
  approximately 25% proteins,
  approximately 7.5% lactic acid,
  approximately 5% minerals and trace elements,
  approximately 1% vitamines, and
  approximately 2% lipids.

Composition A and/or B may comprise at least one diamide compound. Preferred diamide compounds are according to the general structure

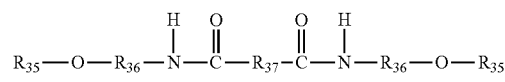

wherein $R_{35}$ is a linear or branched, saturated or unsaturated alkyl chain with 1 to 12 C atoms which may be substituted with hydroxy and/or alkoxy groups, preferably $R_{35}$ is linear or branched, saturated or unsaturated alkyl chain with 1 to 12 C atoms which may be substituted by 1 to 3 substituents selected from a hydroxy group and C1 to C6 alkoxy group, more preferably $R_{35}$ is a unsubstituted alkyl group with 1 to 12 C atoms, and alkyl group with 2 to 12 C atoms substituted by one or two hydroxyl groups, by one alkoxy group with 1 to 6 C atoms or by one hydroxyl and one alkoxy group with 2 to 6 C atoms, $R_{36}$ is linear or branched alkyl chain with 1 to 5 C atoms, preferably linear or branched alkyl chain with 2 to 5 C atoms and more preferably an alkyl chain with 2 to 3 C atoms, and $R_{37}$ linear or branched, saturated or unsaturated alkyl chain with 1 to 22 C atoms, preferably linear or branched, saturated or unsaturated alkyl chain with 11 to 22 C atoms.

Preferred individual diamide compounds are the ones according to the formula A to G.

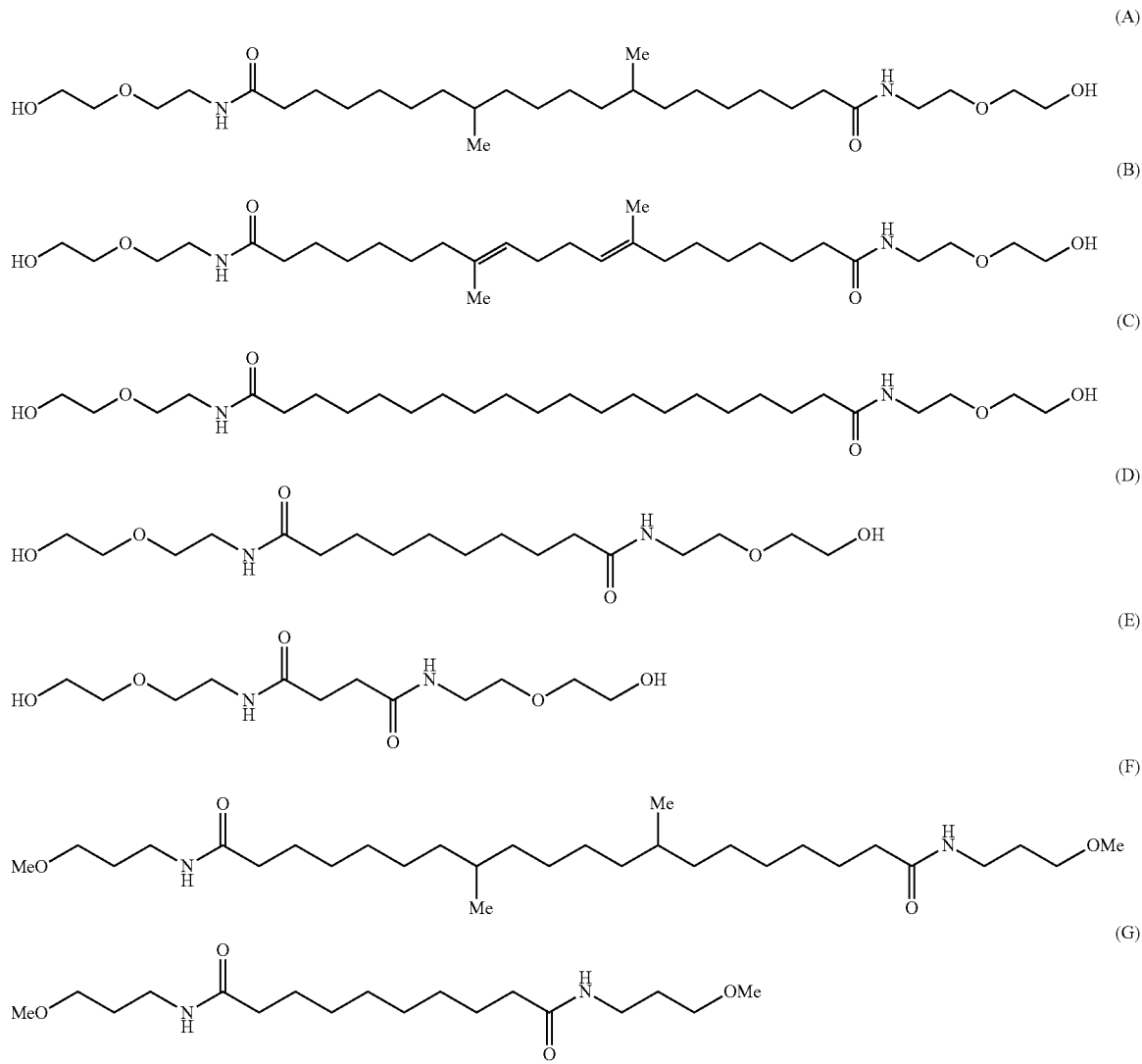

Particularly preferred diamide compound is the compound F which is bis (methoxypropylamido)isodocosane and commercially available from Kao Corporation—Japan.

Concentration of diamide compounds in the compositions A and/or B of the present invention is in the range of 0.001 to 5%, preferably 0.002 to 3% more preferably 0.005 to 2% and most preferably 0.01 to 1% by weight calculated to total of the compositions A or B.

Compositions A and/or B may further comprise one or more dipeptide. Non-limiting examples to the suitable dipeptides are the ones commercially available and known with their INCI name as Dipeptide-1, Dipeptide-2, Dipeptide-3, Dipeptide-4, Dipeptide-5, Dipeptide-6, Dipeptide-7, Dipeptide-8, and carnosine. The most preferred is carnosine and is containing β-alanin and L-histidine.

Concentration of at least one dipeptide is in the range of 0.01 to 5%, preferably 0.05 to 3% and more preferably 0.1 to 2.5% and most preferably 0.2 to 1.5% by weight calculated to the total of the compositions A or B.

Composition A comprises at least one oxidizing agent, preferably at a concentration of at least 0.1% by weight calculated to total of composition A, preferably between 0.25 and 6% and more preferably 0.5 and 5% and most preferably 0.5 and 4% and in particular 1 to 3% by weight calculated to total of composition A.

In principal any oxidizing agent is suitable such as hydrogen peroxide, urea peroxide, melamine peroxide and perborate salts. The most preferred is hydrogen peroxide.

Composition A can further comprise ingredients commonly used in compositions comprising oxidizing agents such as stabilizers for peroxide compounds such as phenacetin, salicylic acid, chelating agents such as etidronic acid, EDTA and/or their salts, organic or inorganic acids such as phosphoric acid, lactic acid, for adjusting pH, surfactants in order to increase miscibility and solubilising aid for water insoluble and/or sparingly soluble substances such as fragrances and anti-foaming agents such as silicone compounds.

Compositions A and B are mixed at a weight ratio of Composition A to Composition B in the range between 10:1 to 1:1, preferably between 7:1 to 1:1, more preferably between 5:1 to 1:1, and most preferably between 3:1 to 1:1. pH of the composition thus obtained and ready to use is in the range between 8 and 12, preferably between 8.5 and 11, more preferably between 9 and 10.5 most preferably between 9 and 10. It has been found out that the viscosity may play an important factor in carrying out the process in a short period of time because the mixed composition is applied only at one part or certain parts of hair. In order to have easy and quick application in order to secure homogeneous effect of the composition and process and as well as rinsing off once the processing time has lapsed, ready to use composition, i.e. after mixing the compositions A and B, preferably has a viscosity in the range between 1000 and 15000 mPa·s., preferably between 1500 and 10000 mPa·s. and more preferably between 2000 and 7500 mPa·s. measured at 20° C. with a rotation viscosimeter, preferably with a Brookfiled viscosimetre at 10 rpm with a spindle 5.

In order to adjust the viscosity of the composition, thickening agents can be used. Suitable and preferred ones are the non-ionic thickeners such as celluose and its derivatives such as hydroxyethyl cellulose, hydroxyethyl ethyl cellulose, hydroxypropyl cellulose, hydroxypropyl methyl cellulose, methyl ethylcellulose, and methyl hydroxyethylcellulose and guar and its derivatives such as hydroxypropy guar. Anionic acrylate based thickeners can also be used.

The following examples are to illustrate the invention but not limit it.

EXAMPLE 1

Composition A

|  | % by weight |
| --- | --- |
| Hydrogen peroxide | 2.0 |
| Phosphoric acid | q.s. to pH 3.0 |
| Phenacetin | 0.1 |
| EDTA | 0.3 |
| Water | q.s. to 100 |

Composition B

|  |  |
| --- | --- |
| Potassium persulfate | 20 by weight |
| Sodium persulfate | 5 |
| Sodium carbonate | 1 |
| Sodium silicate | 10 |
| Diatomaceous Earth | 60 |
| Calcium sulfate | 4 |

The above compositions A and B were mixed at a weight ratio of 3:1 (A:B) and the ready to use composition had a pH of 9.5.

The above composition was applied to the grown natural hair having a medium blonde colour after mixing as given above onto previously light blonde coloured hair. The hair was coloured approximately 6 weeks before the current leveling process. After processing of 5 min the hair was rinsed of and dried with a hair drier.

It was observed that the hair colour was more homogeneous and the colour of the re-growth area was much closer to the lengths. Additionally, volunteers, 5 people, were asked if they had any scalp problems during and also after the treatment, no negatives were mentioned. The same question was asked again 3 days after the leveling service and no complaints were noted.

Similar results were observed with the following examples.

EXAMPLE 2

Composition A

|  | % by weight |
| --- | --- |
| Hydrogen peroxide | 3.0 |
| Phosphoric acid | q.s. to pH 3.0 |
| Sodium laureth sulphate | 2.0 |
| Cetearyl alcohol | 1.0 |
| Phenacetin | 0.1 |
| EDTA | 0.3 |
| Water | q.s. to 100 |

Composition B

|  | % by weight |
| --- | --- |
| Hydroxyethylcellulose | 1.50 |
| Cellulose gum | 3.00 |
| Tetrasodium EDTA | 2.00 |
| Sodium carbonate | 1.00 |
| Ammonium persulfate | 20.00 |
| Potassium persulfate | 20.00 |
| Sodium metasilicate | 10.00 |
| Diatomaceous Earth | 39.50 |
| Polyquaternium - 10 | 0.50 |
| Calcium chloride | 3.00 |

The above compositions A and B were mixed at a weight ratio of 3:1 (A:B) and the ready to use composition had a pH of 9.5.

EXAMPLE 3

Composition A

|  | % by weight |
| --- | --- |
| Hydrogen peroxide | 4.0 |
| Cetearyl alcohol | 1.0 |
| Ceteareth-20 | 0.5 |
| Phosphoric acid | q.s. to pH 3.0 |
| Phenacetin | 0.1 |
| EDTA | 0.3 |
| Water | q.s. to 100 |

Composition B

|  | % by weight |
| --- | --- |
| Hydroxyethylcellulose | 1.40 |
| Cellulose gum | 3.20 |
| Xanthan gum | 0.30 |
| Tetrasodium EDTA | 2.00 |
| Sodium carbonate | 1.00 |
| Ammonium persulfate | 20.00 |
| Potassium persulfate | 20.00 |
| Sodium metasilicate | 10.20 |
| Corn starch | 1.10 |
| Diatomaceous Earth | 36.30 |
| Calcium sulphate | 2.80 |
| Polyquaternium - 10 | 0.10 |
| Silica* | 1.00 |
| Synthetic fluorphologopite** | 1.00 |

*Aerosil 380
**Synthetic fluorphologopite used is commercially available from Merck with a particle size distribution in the range of 5 to 45 μm.

The above compositions A and B were mixed at a weight ratio of 2:1 (A:B) and the ready to use composition had a pH of 9.7.

The invention claimed is:

1. A method for levelling colour of hair comprising at least two parts wherein one part being the part not closer to scalp which is artificially colour changed to a lighter colour by means of lightening and/or colouring and/or bleaching than the other part closer to scalp which is undamaged and has its natural colour, characterised in that hair is optionally shampooed and optionally towel dried and the part directly at the scalp, preferably undamaged and having its natural colour, is applied a composition resulting from mixing two compositions, A and B, prior to application, wherein composition A is an aqueous composition and comprises at least one oxidizing agent and has an acidic pH, between 2 and 5 and composition B is a substantially anhydrous composition and comprises at least one compound with bleaching effect, and composition thus obtained has a pH between 8 and 12, and processed for up to 10 min, at a temperature between 20 and 45° C., and rinsed off from hair and hair is optionally dried.

2. A method according to claim 1 wherein composition B comprises at least one compound with bleaching effect at a concentration between 5 and 85% by weight calculated to total of composition B and selected from peroxides and ammonium salts and their mixtures.

3. A method according to claims 1, wherein composition B comprises peroxides at a total concentration between 5 and 80% by weight and ammonium salts at a concentration between 0.1 and 10% by weight, both are calculated to total of composition B.

4. A method according to claim 1, wherein composition B comprises at least one lipophilic ingredient.

5. A method according to claim 1, wherein composition B comprises at least one polymer selected from non-ionic and cationic ones.

6. A method according to claim 1, wherein composition B comprises at least one calcium salt.

7. A method according to claim 1, wherein composition B comprises at least one direct dye.

8. A method according to claim 1, wherein composition A comprises at least one oxidizing agent, of hydrogen peroxide at a concentration between 0.5 and 6% by weight, calculated to total of composition A.

9. A method according to claim 1, wherein composition A comprises at least one surfactant selected from non-ionic, anionic, cationic and amphoteric ones, and their mixtures at a concentration between 0.1 and 15% by weight calculated to total of composition A.

10. A method according to claim 9 characterised in that wherein composition A comprises at least one surfactant selected from non-ionic and anionic ones, and their mixtures.

11. A method according to claim 1, wherein composition A comprises at least one fatty alcohol.

12. A method according to claim 1, wherein compositions A and/or B comprises at least one compound selected from thickeners, aminopropyl dimethyl polysiloxane/polyethyl oxazoline copolymers, ceramides, sterols, ubiquinones, yoghurt powder, diamide compounds and dipeptides.

13. A method according to claim 1, wherein compositions A and B are mixed at a weight ratio between 10:1 and 1:1.

14. A method according to claim 1, wherein the viscosity of the composition after mixing of compositions A and B at a weight ratio between 10:1 and 1:1 is in the range of 1000 and 15000 mPa·s measured with a Brookfield viscosimeter at 20° C. with Spindle 5 at 10 rpm.

* * * * *